United States Patent
Buchberger

(10) Patent No.: US 11,555,822 B2
(45) Date of Patent: Jan. 17, 2023

(54) METHOD AND KIT FOR SAMPLE PREPARATION AND ENDOTOXIN DETERMINATION

(71) Applicant: Andreas Buchberger, Zeitlarn (DE)

(72) Inventor: Andreas Buchberger, Zeitlarn (DE)

(*) Notice: Subject to any disclaimer, the term of this patent is extended or adjusted under 35 U.S.C. 154(b) by 0 days.

(21) Appl. No.: 17/534,650

(22) Filed: Nov. 24, 2021

(65) Prior Publication Data

US 2022/0082577 A1   Mar. 17, 2022

Related U.S. Application Data

(62) Division of application No. 16/760,274, filed as application No. PCT/EP2018/079990 on Nov. 2, 2018, now Pat. No. 11,199,554.

(30) Foreign Application Priority Data

Nov. 9, 2017  (EP) .................................... 17200857

(51) Int. Cl.
*G01N 33/92* (2006.01)
*G01N 1/40* (2006.01)
*B01J 20/281* (2006.01)

(52) U.S. Cl.
CPC ............ *G01N 33/92* (2013.01); *G01N 1/4005* (2013.01); *G01N 1/4077* (2013.01); *G01N 30/482* (2013.01); *G01N 2400/50* (2013.01)

(58) Field of Classification Search
CPC .... G01N 33/92; G01N 1/4005; G01N 1/4077; G01N 30/482; G01N 2400/50; G01N 33/579
See application file for complete search history.

(56) References Cited

U.S. PATENT DOCUMENTS

| 10,585,097 B2 | 3/2020 | Alexander et al. |
| 2003/0040613 A1 | 2/2003 | Bishop et al. |

(Continued)

FOREIGN PATENT DOCUMENTS

| EP | 3124976 A1 * | 2/2017 | ............... G01N 1/38 |
| WO | 9522556 A1 | 8/1995 | |

OTHER PUBLICATIONS

"EndoTrap® Standard Application Protocol", version 06, 2012, Hyglos GmbH, pp. 1-10. [retrieved from internet on Aug. 27, 2021].

(Continued)

*Primary Examiner* — Jennifer Wecker
*Assistant Examiner* — Michael Paul Shimek
(74) *Attorney, Agent, or Firm* — Simmons Perrine Moyer Bergman PLC

(57) ABSTRACT

The invention relates to a method for preparation of a sample (10) of a formulation (11) for subsequent endotoxin determination, the formulation (11) suspected of comprising an endotoxin, the formulation (11) preferentially being a pharmaceutical formulation. The method comprises the following steps: application of the sample (10) to an endotoxin-free centrifugation column (2) containing a size exclusion chromatography matrix (5) that has been equilibrated with a suitable equilibration buffer (6) and elution of a flow through (15) of the sample by centrifugation, which flow through (15) can then be used for endotoxin determination. The equilibration buffer (6) is selected according to a subsequently used method of endotoxin determination, the equilibration buffer (6) only containing components not interfering with subsequently used method of endotoxin determination. Furthermore, the invention relates to a kit (20) for preparation of a sample (10).

18 Claims, 3 Drawing Sheets

(56) References Cited

U.S. PATENT DOCUMENTS

2017/0227529 A1 8/2017 Buchberger
2019/0353648 A1 11/2019 Reich et al.

OTHER PUBLICATIONS

Bio-Rad: Bio-Spin® Columns with Bio-Gel® P-6. [retrieved from internet on Aug. 25, 2021] published on Sep. 5, 2014 as per Wayback Machine.
Chapter 2.6.14 of the European Pharmacopoeia, 9th Edition, Chapter 2.6.14. "Bacterial Endotoxins".
Chapter 2.6.30 of European Pharmacopoeia, 9th Edition, Chapter 2.6.30. "Monocyte-Activation Test".
Chapter 2.6.8 of the European Pharmacopoeia, 7th and 10th Edition, Chapter 2.6.8. "Pyrogens".
Chapter 5.1.10. of European Pharmacopoeia, 9th Edition, Chapter 5.1.10. "Guidelines for Using the Test for Bacterial Endotoxins".
Grallert et al. in Nature Methods, Oct. 2011, pp. iii-v, "EndoLISA: a novel and reliable method for endotoxin detection".
Harald Schwarz et al in Scientific Reports 7:44750 (2017), pp. 1-11.
Johannes Reich, Pierre Lang, Holger Grallert, Hubert Motschmann in Biologicals 44 (2016), pp. 417-422 "Masking of Endotoxin in surfactant samples: Effects on Limulus-based detection systems".
Ongkudon C.M. et al: "Chromatographic removal of endotoxins: a biopress engineer's perspective", ISRN Chromatogr., vol. 2012, 2012, pp. 1-9, XP055437755, the whole document.
Ouellette T. et al: "Production and purification of refolded recombinant human IL-7 from inclusion bodies", Prot. Express. Purificat., vol. 30, No. 2, Aug. 2003 (Aug. 2003), pp. 156-166, XP004439523, the whole document.
Sandle T.: "Removal of endotoxin from protein in pharmaceutical processes", Am. Pharmaceut. Rev., No. Endotoxin Suppl., Sep. 2016, pp. 8-11.
Saraswat M. et al: "Preparative purification of recombinant proteins: Current status and future trends", Biomed Res. Int., vol. 2013, 2013, pp. 1-18, XP055429379, the whole document.
Williams K.L. in American Pharmaceutical Review. Endotoxin Supplement 2014 "Endotoxin Test Concerns of Biologics Part II: Developing New Tools".
Wunderlich et al. in BMC Pharmacology & Toxicology 15:50(2014), pp. 1-7 "Pyrogen detection methods: Comparison of bovine whole blood assay (bWHB) and monocyte activation test (MAT)".

* cited by examiner

METHOD AND KIT FOR SAMPLE PREPARATION AND ENDOTOXIN DETERMINATION

CLAIM OF PRIORITY

The present application is a divisional application of the U.S. application Ser. No. 16/760,274 filed Apr. 29, 2020, now U.S. patent Ser. No. 11/199,554, issued Dec. 14, 2021, which claims priority to International Application PCT/2018/079990, filed Nov. 2, 2018, which in turn claims priority to European Application EP17200857.5, filed Nov. 9, 2017, which are incorporated by reference.

FIELD OF THE INVENTION

The present invention relates to a sample preparation method unmasking endotoxins in formulations, especially pharmaceutical formulations or the like, to be able to detect endotoxins that may be present within the formulation but undetectable using conventional endotoxin testing methods. The invention also relates to a sample preparation kit unmasking endotoxins in formulations, thereby rendering them detectable.

BACKGROUND OF THE INVENTION

Endotoxins are the outer membrane components of Gram-negative bacteria. These amphiphilic molecules, also known as lipopolysaccharides, represent a very heterogeneous class of substances. In the following description the terms endotoxin and lipopolysaccharide are used synonymously and lipopolysaccharides are generally referred to as LPS. However, the hydrophobic lipid A part of the different LPS is highly conserved and is therefore used as recognizable signal in the established endotoxin detection methods. Drugs that need to be administered parenterally must be tested for endotoxin impurities in accordance with Pharmacopoeia. The Pharmacopoeia is a legal and scientific benchmark for pharmaceutical standards in Europe and other countries. These pharmaceutical standards are especially listed in the European Pharmacopoeia (Ph.EU), the United States of America Pharmacopoeia (Ph.US), the Japan Pharmacopoeia (Ph.JP), etc. The pharmaceutical standards also apply to invasive medical devices.

The European Pharmacopoeia lists different methods for the detection of endotoxins. Chapter 2.6.14 of the European Pharmacopoeia, 9th Edition, Chapter 2.6.14. "Bacterial Endotoxins" describes different methods based on Limulus amoebocyte lysate, further referred to as LAL, especially a gel-clot assay, a turbidimetric assay and a kinetic chromogenic assay.

Chapter 2.6.30 of European Pharmacopoeia, 9th Edition, Chapter 2.6.30. "Monocyte-Activation Test" describes a cellular test based on human monocytes, e. g. whole blood, peripheral Blood Mononuclear Cells (PBMCs) or monocyte derived cell lines. This test replaces the "Rabbit Pyrogen Test", which is described in European Pharmacopoeia, 9th Edition, Chapter 2.6.8. "Pyrogens", and which, due to animal welfare reasons, is only allowed in Europe in very well-founded cases.

Chapter 5.1.10. of European Pharmacopoeia, 9th Edition, Chapter 5.1.10. "Guidelines for Using the Test for Bacterial Endotoxins" describes alternative test methods that use the recombinant Factor C of the horseshoe crab as primary LPS receptor. Factor C is also the primary LPS receptor in the LAL reagent.

All mentioned test systems are commercially available from different companies. All detection methods, with one exception, are so-called homogeneous test procedures. In homogeneous tests, a sample is directly combined with the assay reagent generating a measurable signal. Heterogeneous assays use a selective solid phase and at least one washing step to separate the solid phase bound analyte from the sample matrix according to the principle of enzyme-linked Immunosorbent based assays (ELISA). Currently only one heterogeneous, solid phase based endotoxin test can be found on the market. This so called EndoLISA test is produced and marketed by the company Hyglos.

The disadvantage of homogeneous test procedures is that components of the sample matrix can interfere with the test or, in the case of cell-based tests, can have a negative effect on the physiology of the cells. These interferences are a common complication during endotoxin detection. Accordingly, the European Pharmacopoeia requires a test for interfering factors for all endotoxin tests. Preparations containing interfering components usually have to be diluted until the negative effect disappears. Therefore, this leads to a reduction of the achievable detection limit and sometimes to the fact that no suitable method is available for detection of endotoxins within the legally prescribed minimum sensitivity range. According to the European Pharmacopoeia requirements, a test result is considered valid if an internal control added to the sample is found in the range of 50% to 200% of the nominal value. As internal control the sample is spiked with a defined amount of LPS standard material.

The only heterogeneous test available on the market is considerably less susceptible to matrix effects, but also has a 10-fold lower sensitivity. This is described by Grallert et al. in Nature Methods, October 2011, pages iii-v, "EndoLISA: a novel and reliable method for endotoxin detection".

The cell-based monocyte activation test is naturally also susceptible to matrix constituents. Due to the lower sensitivity higher sample concentrations have to be used and the reactivity/vitality of the cells in culture is often strongly and complexly influenced during the long incubation periods of 4 to 18 hours as described by Wunderlich et al. in BMC Pharmacology & Toxicology 15:50(2014), pages 1-7 "Pyrogen detection methods: Comparison of bovine whole blood assay (bWHB) and monocyte activation test (MAT)".

Another important problem of the currently used testing methods is a phenomenon that is referred to as "Low Endotoxin Recovery" in recent literature. This phenomenon is further referred to as LER and is described by Johannes Reich, Pierre Lang, Holger Grallert, Hubert Motschmann in Biologicals 44 (2016), pages 417-422 "Masking of Endotoxin in surfactant samples: Effects on Limulus-based detection systems". LER describes the observation that formulations containing chelators for bivalent cations in combination with detergents change the endotoxin in such a way that it can no longer be detected by the established methods prescribed in the Pharmacopoeia. The molecular mechanism underlying this problem is probably that the stabilizing salt bridges in the LPS complex are broken down by chelators, thereby dissociating or solubilizing the LPS complex in the presence of detergent in concentrations above the critical micelle concentration (cmc). Such detergent solubilized single LPS molecules which are integrated into detergent micelles, cannot be detected or can only be detected very weakly by the available methods as described by Harald Schwarz et al. in Scientific Reports 7:44750 (2017), pages 1-11.

The formulations or compositions of modern protein pharmaceuticals, e. g. hormones, therapeutic antibodies, enzymes, often contain phosphate or citrate buffers in combination with detergents from the Tween or Span series. Phosphate or citrate buffers are chelators for ions, especially for bivalent cations. If such undiluted formulations are spiked with endotoxin—this is especially called "hard-spike"- and kept at 4° C. or room temperature for longer periods of time, the added endotoxin cannot or can hardly be detected. This means that even a high endotoxin contamination in a formulation can no longer be detected due to the masking of the endotoxin. Nevertheless, the endotoxin can still be dangerous for the patient receiving this formulation. The significance of the tests prescribed in the Pharmacopoeia is thus questioned. The regulatory authorities like Food and Drug Administration (FDA) or European Medicines Agency (EMA) have for some time now been requesting "hard-spike" experiments for new approval procedures as well as for imported drugs. In case Low Endotoxin Recovery (LER) is observed in a drug formulation, the pharmaceutical company is asked to provide alternative methodology verifying the validity of the test results under "hard spike" conditions.

A possible methodical approach to eliminate this problem is to restore the solubilized LPS to the aggregate form, i.e. to reverse the reaction leading to inactivation of the LPS (aggregate form↔monomer form). To achieve this, the following two methods are currently used:

The method described in EP 2 955 518 A1 uses a highly specific amphiphilic compound, especially a lauryl alcohol, and various other additives to restore the LPS to its aggregate form. The disadvantage of this method is that according to the principle of a multi-dimensional screening, many combinations of components have to be evaluated at several different concentrations. This method is very time-consuming and requires several rounds of optimization. A respective screening should be repeated for each new pharmaceutical active ingredient, furthermore referred to as API and for each new formulation of such API. Furthermore, it is also not possible to simply transfer a specifically developed method from one endotoxin determination method to another.

The method described in EP 3 124 976 A1 uses dialysis to create conditions to transform the solubilized LPS into complex form. To influence the equilibrium between the solubilized, inactive LPS and the aggregate LPS, high concentrations of magnesium ions, for example 50 mM, are used. This method has the disadvantage that dialysis is complex and time-consuming, especially for detergents with low critical micelle concentration (cmc). Depending on the formulation of the sample, a more or less strong dilution takes place during dialysis. The number of samples or conditions that can be tested in parallel is limited. It is not described how or whether the method can easily be applied to other formulations or other active pharmaceutical ingredients.

In addition to the combination of chelators and detergents, endotoxin can also be neutralized by proteins with basic isoelectric points or proteins with distinctly basic clusters as described by Williams K. L. in American Pharmaceutical Review. Endotoxin Supplement 2014 "Endotoxin Test Concerns of Biologics Part II: Developing New Tools". Monoclonal antibodies can also have corresponding properties. Therefore, sometimes more than one active masking principle must be addressed during reconstitution of LPS in order to achieve a high recovery rate.

SUMMARY OF THE INVENTION

Based on the described prior art and the mentioned limitations of the available sample preparation and endotoxin determination methods, the objective is to develop a sample preparation method that allows a reliable and reproducible unmasking of endotoxins contained in formulations, especially in pharmaceutical formulations.

The objective is achieved by a sample preparation method to be used prior to an endotoxin testing and by an endotoxin determination method according to the features of the independent claims. Furthermore, the objective is achieved by a kit comprising components for a sample preparation prior an endotoxin testing according to the features of the independent device claim.

The method according to the invention describes a sample preparation step for formulations suspected of containing endotoxin/LPS, which endotoxin/LPS might be masked by other components of the formulations. These other components interfere with the known endotoxin detection and/or determination methods. The method according to the invention prepares a sample of the formulation to be tested in such a way that all known endotoxin determination methods can then be successfully used for reliable results. The sample preparation method especially uses the principle of size exclusion chromatography, thereby allowing the elimination of interfering factors from samples of the formulation to be analysed with state-of-the art endotoxin detection methods. The method for preparation of a sample of a formulation for subsequent endotoxin determination, the formulation suspected of comprising an endotoxin, comprises the following steps: an endotoxin-free centrifugation column containing a size exclusion chromatography matrix is equilibrated with a suitable equilibration buffer. Then a sample of the formulation to be tested for endotoxin is applied onto the column. The centrifugation column with the sample is then centrifuged and the flow through is collected. This flow through can then be used for endotoxin testing and/or endotoxin determination. Preferably the equilibration buffer is selected according to the subsequently used method of endotoxin determination. Especially the equilibration buffer only contains components that are not interfering with the subsequently used method of endotoxin determination.

The formulation may comprise components leading to inhibition or non-specific activation of the endotoxin detection method. These inhibitory components are removed by the method described above. The formulation may, for instance, comprise a detergent, a buffer substance and an active pharmaceutical ingredient (API) or a protein or an antibody, masking the endotoxin and/or interfering with the endotoxin testing methods. This is especially problematic for formulations comprising a detergent in a concentration above its critical micelle concentration (cmc), especially if the detergent is a member of the group of Tween or Span detergents. Span Detergents are nonionic surfactants, for example Sorbitane monooleate, Sorbitane trioleate. Tween detergents are non-ionic viscous liquids, for example Polyethylene glycol sorbitan monolaurate, Polyoxyethylenesorbitan monopalmitate, Polyethylene glycol sorbitan monooleate. Micelle formation is especially problematic for formulations comprising Polyethylene glycol sorbitan monolaurate (Tween 20) in a concentration above 60 micromolar (μM) or Polyethylene glycol sorbitan monooleate (Tween 80) in a concentration above 12 micromolar (μM).

Furthermore, buffering components with chelating properties for bivalent cations interfere with the stability of high-molecular LPS aggregates that are detected by the endotoxin testing methods. Furthermore, buffering components selected from the group of phosphate, citrate or histidine are often used for pharmaceutical formulations, for example antibody preparations or the like. These buffering components also interfere with endotoxin testing and therefore they need to be removed prior to endotoxin testing.

The components interfering with the endotoxin tests are usually comparatively small molecules with sizes less than 1,500 Dalton. After application of the sample of the formulation onto the column containing a suitable equilibrated size exclusion chromatography matrix (resin), these small molecules contained in the formulation can instantly spread into the gel matrix. The endotoxin or LPS is usually present as a high-molecular complex or aggregate, which remains in the exclusion volume of the column. The exclusion volume of the gel matrix used in the column is selected in such a way that monomeric LPS with a reported molecular weight between 6 Kilodalton and 18 Kilodalton also remains in the exclusion volume. The centrifugation step separates monomeric LPS as well as the large LPS complex or LPS aggregate from the small components of the formulation. Meanwhile the small components remain within the gel matrix, the large LPS complex or aggregate can be found after the centrifugation step in the flow through. Because excess equilibration buffer is removed from the column prior to the application of the sample as described below, the volume of the flow through preferentially corresponds exactly to the volume of the applied sample. This means, in particular, that no dilution takes place. The flow through contains the high molecular weight components of the sample, whereby the high molecular weight components are now buffered in equilibration buffer or particular effectors can be added.

The choice of the suitable equilibration buffer allows a complete change of the buffering system within the sample of the formulation. Alternatively, only individual components of the buffer within the sample of the formulation can be replaced.

According to a preferred embodiment of the invention, any excess equilibration buffer is removed from the column prior to the application of the sample onto the column to ensure that the sample volume is not increased by the centrifugation step. Especially, equilibration buffer is only removed from the void volume of the column, whereas the equilibration buffer is strongly retarded within the matrix structure due to high water binding force of the hydrophilic gel matrix. This equilibration buffer removing centrifugation step is preferentially performed with the same applied centrifugation force used subsequently for collecting the flow through of the sample. For example, if the gel matrix is centrifuged dry by a centrifuge at 1,000 g, the centrifugation of the sample is also performed at 1,000 g. According to a preferred embodiment of the invention, the centrifugation step for collecting the flow through comprising the LPS and/or the centrifugation step for removing excess equilibration buffer is/are performed at a centrifugal force of more than 200 g, especially at more than 1,000 g, preferentially at more than 1,500 g, especially at 1,800 g.

Solubilized LPS describes individual LPS molecules that are integrated into detergent micelles. This masks the LPS in such a way that the endotoxin testing methods are rendered invalid.

If solubilized LPS is present within the sample applied to the gel matrix of the column, the detergent is separated from the LPS because of the dynamic equilibrium between the detergent monomer and the detergent micelles. The detergent monomers have a molecular weight of 1,300 Dalton or less. Therefore, the detergent monomers spread into the gel matrix or resin and are not further available for micelle formation. As a result, the LPS is released from the micelles during the application of the sample of the formulation into the column and the subsequent centrifugation step and can now re-aggregate with other LPS molecules into high-molecular LPS complexes or LPS aggregates. This LPS aggregation especially takes place in the presence of bivalent cations, reversing the inhibiting properties of bivalent cation chelators on endotoxin testing methods.

The size exclusion chromatography matrix is preferentially an uncharged, crosslinked, hydrophilic gel matrix, especially a crosslinked polyacrylamide gel matrix. The exclusion volume of the gel matrix or resin is selected in such a way that monomeric LPS with a molecular weight ranging from 6 Kilodalton to 18 Kilodalton remains in the exclusion volume, meanwhile the small buffer components contained in the formulation are distributed within the gel. Preferentially the size exclusion chromatography gel matrix or resin has a size exclusion volume or exclusion cut-off within the range of 2,000 Dalton to 20,000 Dalton, especially between 4,000 Dalton to 7,000 Dalton, most preferred below 6,000 Dalton.

According to one embodiment of the invention the size exclusion chromatography gel matrix or resin has an average particle size between 5 µm and 250 µm, preferably between 5 µm and 180 µm, especially between 5 µm and 50 µm. It is especially important that the gel matrix or resin used for the method has a high mechanical stability so that the material does not collapse when centrifugation forces of up to 1,800 g are applied.

Furthermore, the gel matrix or resin must show no or only very low interaction with LPS to ensure a good recovery of LPS from the column. These criteria are met by different commercially available gel matrix or resin materials listed in the table 1 below.

TABLE 1

Suitable gel materials for the sample preparation method

| Product name | Company | Matrix | wet bead size | fractionation range |
| --- | --- | --- | --- | --- |
| Biogel P4 | BioRad | polyacrylamide beads | 45-90 µm | 800-4,000 Da |
| Biogel P6 | BioRad | polyacrylamide beads | 90-180 µm | 1,000-6,000 Da |
| Superdex 30 | GE Healthcare Life Sciences | cross-linked agarose and dextran | 24 µm-44 µm | 1,000-5,000 Da |

The size of the column is selected according to the volume of the gel matrix or resin used. Preferentially about 1 ml to 1.5 ml gel matrix or resin is packed in a column. The maximum sample volume applied to the column should not exceed 10-20% of the bed volume, e. g. when using a 1 ml bed volume, samples of up to 200 µl can be applied.

Before use the gel matrix or resin should be equilibrated with a suitable buffer system. Thereby two to three column volumes or bed volumes of the equilibration buffer should be used. The equilibration buffer should only contain components not interfering with the endotoxin testing method to be subsequently used. Therefore, the equilibration buffer is selected according to the subsequently used method of endotoxin determination.

According to a preferred embodiment of the invention, the equilibration buffer comprises a buffer substance that is different from the buffer used in the formulation that is to be tested for endotoxin and furthermore, the equilibration buffer comprises at least one bivalent cation. Especially the equilibration buffer may comprise $Ca^{2+}$ and/or $Mg^{2+}$ as bivalent cations. The concentration of the $Ca^{2+}$ and/or $Mg^{2+}$ cations is preferably within a range between 1 mM and 100 mM, preferably between 1 and 50 mM, more preferably between 20 and 50 mM. The pH value of the equilibration buffer should be around neutral, preferably between 6.0 and 8.5, most preferably between 7.0 and 8.0.

Furthermore, the equilibration buffer optionally comprises an amphiphilic substance in a concentration below its critical micelle concentration. This low concentration of the optional amphiphilic substance avoids the problem of masking the endotoxin by integration of the endotoxin into detergent micelles but helps stabilizing monomeric LPS in solution. According to another preferred embodiment, the concentration of the amphiphilic substance should be equal or below its solubility threshold in the equilibration buffer system. Especially the amphiphilic substance is selected from a group consisting of Lauryl alcohol, Tween 20 (Polyethylene glycol sorbitan monolaurate), Polypropylenglycol or SDS (sodium dodecyl sulfate).

A suitable first example of an equilibration buffer composition may contain: 20 mM Tris/HCl at pH 7.4; 50 mM NaCl and 1 mM to 5 mM $Ca^{2+}$ or $Mg^{2+}$. A suitable second example of an equilibration buffer composition may contain: 20 mM HEPES (4-(2-hydroxyethyl)-1-piperazineethanesulfonic acid) at pH 7.2; 50 mM NaCl and 20 mM to 50 mM $Ca^{2+}$ or $Mg^{2+}$.

Therefore, monomeric as well as aggregated LPS can be eluted by a second centrifugation step, meanwhile the small components forming the buffer of the formulation remain within the column. A gel matrix or resin based on cross-linked polyacrylamide is particularly suitable for the method according to the invention, because of its hydrocarbon backbone this material has a partially hydrophobic character and at the same time this material can extensively form hydrogen bonds with water molecules via the acrylic acid amide side chains. Therefore, in addition to the distribution principle described above, these properties provide an adsorptive component assisting the separation of small amphiphilic substances. Based on the mechanism described above it is clear, that especially for formulations comprising comparatively low LPS concentrations in the range of Nanograms per Millilitre (ng/ml) the system takes a certain amount of time to re-form the LPS complexes or LPS aggregates that can be measured with the known endotoxin methods. The kinetics of this aggregation process also depends on the composition of the flow through after the centrifugation step.

The invention furthermore relates to a method for endotoxin determination whereby a sample of a formulation suspected of comprising an endotoxin is analysed, wherein the formulation is preferentially a pharmaceutical formulation. A sample of the formulation is applied to an endotoxin-free centrifugation column containing a size exclusion chromatography matrix that has been equilibrated with a suitable equilibration buffer. This sample loaded column is then centrifuged at a certain speed and a defined time period. The flow through is collected and used for testing for endotoxin by using a suitable method. According to a preferred embodiment the collected flow through is incubated at a certain temperature for a defined period of time prior to endotoxin testing to allow completion of self-assembly into LPS aggregates.

As has been explained beforehand in connection with the sample preparation method, the composition of the equilibration buffer is selected according to the subsequently used method of endotoxin determination and/or excess equilibration buffer is removed from the gel matrix of the column by a first centrifugation step.

Alternatively, or in addition to the described characteristics the method of endotoxin determination can show one or more characteristics and/or properties of the sample preparation method described before.

According to a preferred embodiment of the invention, the preparation of a sample of a formulation presumably containing an endotoxin masked by interfering components contained in the formulation, is characterized by the following steps:

A suitable gel matrix material is placed in a small endotoxin free chromatography column and equilibrated with a suitable equilibration buffer. Preferentially the composition of the equilibration buffer is selected according to the subsequently used method of endotoxin determination.

The gel material is centrifuged dry by a centrifuge at 1,800 g, the flow through of excess equilibration buffer is discarded.

A sample of the formulation to be tested is applied to the dry-centrifuged column.

The column is then centrifuged once again at 1,800 g, the flow through is collected.

Prior to using the collected flow through for subsequent endotoxin testing, the collected flow through can be incubated for a certain period of time before the endotoxin testing to allow equilibration between monomeric LPS and aggregated LPS, especially to allow completion of self-assembly into LPS aggregates.

The thus incubated flow through can be used directly or in a diluted form with an endotoxin determination method described previously.

The effectiveness of the method in unmasking a solubilized endotoxin has been shown by spiking samples with a known concentration of endotoxin and incubation of this positive control for a certain time at a defined temperature. If such a spiked sample is used with an endotoxin determination method described previously, no, or only a reduced amount of endotoxin may be measured depending on the buffer used as basis for the sample, which may contain components masking the endotoxin. After treating the spiked sample with the method described above, the endotoxin contained in the spiked sample can now be quantified correctly.

The invention furthermore relates to a method allowing evaluation of Low Endotoxin Recovery (LER) effects in a given pharmaceutical formulation and/or elaboration of a composition of a suitable equilibration buffer. To achieve this, the method comprises the following steps: First a sample of an undiluted pharmaceutical formulation is spiked with a known activity of lipopolysaccharide (LPS) standard. An aliquot of this spiked sample is used for endotoxin testing. A Low Endotoxin Recovery (LER) effect is indicated if the spiked sample shows a test result corresponding to less than 50% of the known activity of the lipopolysaccharide (LPS) standard spiked into the sample. From a sample with a proven Low Endotoxin Recovery (LER) effect, at least two aliquots are applied to at least two endotoxin-free centrifugation columns, whereby each centrifugation column contains a size exclusion chromatography matrix and has been equilibrated and/or conditioned with a different equilibration buffer. The centrifugation columns with the applied aliquots of the spiked sample are then centrifuged and the flow through from each centrifugation column is collected. The different flow throughs are then subjected to endotoxin testing in order to test for lipopolysaccharide (LPS) recovery. The sample with the best result, e.g. the highest recovered activity of the lipopolysaccharide (LPS) standard, shows which equilibration buffer is best suited for testing the given pharmaceutical formulation. The results are especially compared to an aliquot of the non-centrifuged spiked sample and a positive water control. Using a suitable centrifuge, up to 72 formulation variants could be evaluated in one run.

Preferentially after spiking the undiluted sample of the given pharmaceutical formulation spiked with a known activity of the lipopolysaccharide (LPS) standard, this spiked sample is incubated for a certain period of time between 1° C. and 37° C. prior to endotoxin testing. Preferably this incubation is done at about 4° C. in a refrigerator or the like or at room temperature, preferentially between 18° C. and 24° C. The incubation time prior to endotoxin testing is at least 1 h, preferred more than 24 h and most preferred between 24 h and 168 h. After incubation the LER effect of the formulation can be evaluated by directly applying the sample to an endotoxin test. This is a so called hard spike experiment. The invention furthermore relates to a kit for the preparation of a sample of a formulation to be used for subsequent endotoxin determination, the formulation suspected of comprising an endotoxin, the formulation preferentially being a pharmaceutical formulation. The kit comprises the following endotoxin-free components:

- at least one centrifugation column or spin column prepacked with a size exclusion chromatography gel matrix or resin OR,
- at least one centrifugation column or spin column and a size exclusion chromatography gel matrix or resin material AND
- an equilibration buffer.

The kit especially comprises all components necessary for performing the methods described above. Additionally, a centrifuge and pipettes and other laboratory equipment(s) are required and must be supplied by the user. These other laboratory equipment(s) is/are not included in the kit. The equilibration buffer is used to equilibrate the gel matrix prior to sample preparation according to the explained method. The kit may further comprise a user manual explaining the method and the individual steps to be performed. The manual might also give examples for the preparation of alternative equilibration buffers. Preferably the equilibration buffer is selected according to the subsequently used method of endotoxin determination. Especially the equilibration buffer only contains components that are not interfering with the subsequently used method of endotoxin determination. Furthermore, the manual might contain explanations and hints for optimizing the equilibration buffer most suited for the selected endotoxin testing method.

Furthermore, the kit may contain an endotoxin sample to be used as positive control. To prove the effectiveness of the methods described above and the kit using these methods, LPS/endotoxin of a known activity can be spiked into a sample of the formulation to be tested prior to application onto the column and subsequent centrifugation. Preferentially the formulation spiked with LPS/endotoxin is then incubated at least for 1 hour, preferentially at least 24 h; most preferred between 24 h and 168 h. The incubation can be performed at a temperature between 0° C. and 37° C. especially in the refrigerator at about 4° C. or at room temperature in the range of 18° C. to 24° C.

If the formulation comprises components masking the LPS and/or otherwise interfering with endotoxin determination, the spiked LPS within the formulation sample is not detectable or detectable only in reduced amounts if this sample is directly used for endotoxin testing without further sample preparation. But if the sample with the LPS spike is treated by the sample preparation method described above, especially if the sample with the LPS spike is applied to the column provided by the kit, the column is then centrifuged and the flow through collected, the LPS can be detected by the conventionally known endotoxin testing methods within the collected flow through.

It should be expressly mentioned at this point that all aspects and variants which have been explained in connection with the methods according to the invention, equally concern or can be partial aspects of the kit according to the invention. Therefore, if the description or the definition of claims contain certain aspects and/or interrelationships and/or effects for the kit based on the invention, this equally applies to the methods according to the invention. Conversely, the same applies, so that all aspects and embodiments which have been explained relating to the kit according to the invention are or may be equally affected by partial aspects of the different methods according to the invention. Therefore, if there is a reference to certain aspects and/or interrelationships and/or effects at one point in the description or also in the definition of claims relating to the kit according to the invention, this equally applies to the methods of sample preparation and/or endotoxin determination in accordance with the invention.

With the methods according to the invention and the sample preparation kit according to the invention, low-molecular components of a formulation interfering with the endotoxin testing methods can be eliminated easily, comprehensively and quickly. Solubilized LPS, which cannot be detected within an untreated sample due to the masking by the interfering components is converted into its active aggregate form and can now be detected and quantitatively measured and/or determined. Thereby, the sample can be used undiluted, allowing for a maximised sensitivity. The sample can especially be validated according to the requirements of the Pharmacopoeia. Furthermore, the methods and the use of the kit are simple, fast, robust, easy to use and suitable for a higher sample throughput and therefore, suitable for routine applications.

Neutralization of LPS/endotoxin by basic proteins cannot be eliminated by the method according to the invention, which does not separate protein and LPS when passing the sample through the column. However, the expert in the technical field is aware of methods that can be combined with the method proposed here. For example, anionic detergents with high critical micelle concentration (cmc) are used to replace the LPS from positively charged protein binding pockets. Especially Sodium Dodecyl Sulfate (SDS) can be used to replace the LPS from positively charged protein binding pockets. Furthermore, polymers with a highly negative charge have proved to be effective, e. g. polyacrylic acid, sodium salt or the like. Finally, commercially available dispersing agents are used. The composition of these dispersing agents has not been published, e. g. PyroSperse from Lonza. According to the manufacturer the dispersing agents use a metallo-modified polyelectrolyte as a principle. These reagents can be easily combined with the method according to the invention by adding them to the collected flow through after the centrifugation step.

The gel filtration columns used in this process can basically use all known gel materials, provided that the physical stability of the matrix permits this.

BRIEF DESCRIPTION OF THE FIGURES

In the following passages, the attached figures further illustrate exemplary embodiments of the invention and their advantages. The size ratios of the individual elements in the figures do not necessarily reflect the real size ratios. It is to be understood that in some instances various aspects of the invention may be shown exaggerated or enlarged to facilitate an understanding of the invention.

Figure 1:
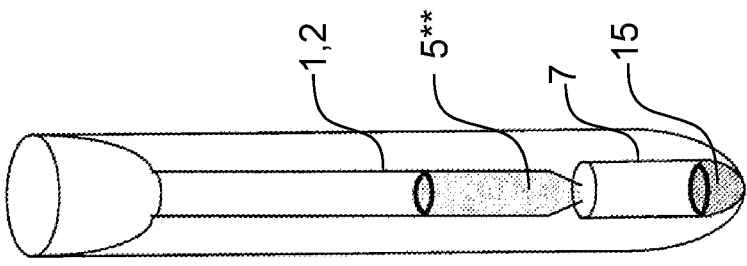
FIGS. 1 and 2 show the preparation of a column provided by the kit and used for the methods according to the invention.

The same or equivalent elements of the invention are designated by identical reference characters. Furthermore, and for the sake of clarity, only the reference characters relevant for describing the respective figure are provided. It should be understood, that the embodiments described are only examples and they are not intended to limit the scope of the disclosure.

DETAILED DESCRIPTION OF THE INVENTION

Figure 2:
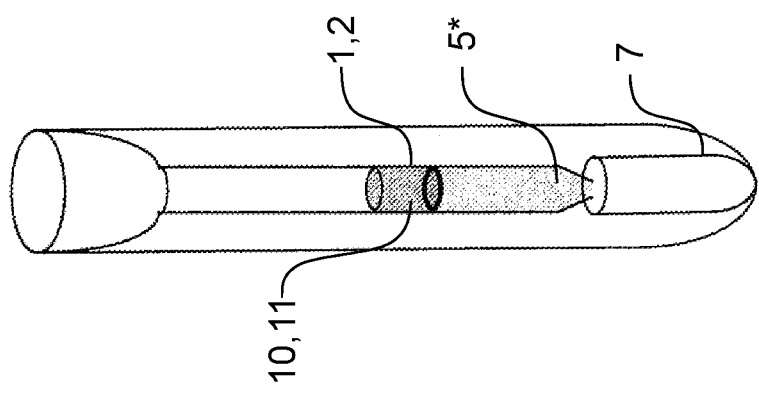
Figure 3:
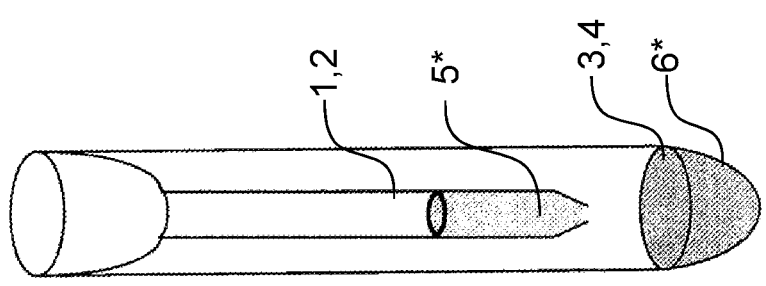
FIGS. 3 and 4 show the application and treatment of a sample.
Figure 4:
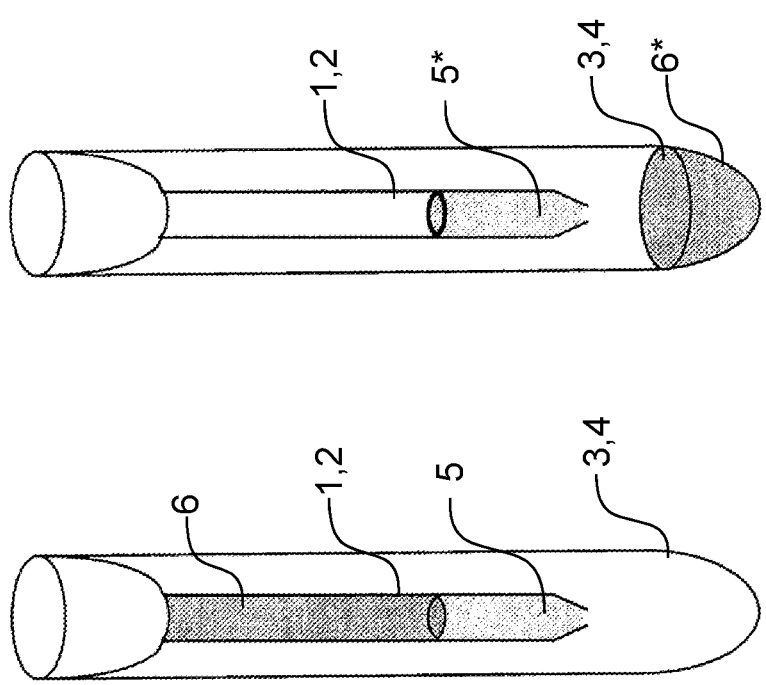

FIGS. 1 and 2 show the preparation of a column 1 provided by the kit and used for the methods according to the invention. FIGS. 3 and 4 show the application and treatment of a sample 10.

The column 1 is especially an endotoxin-free centrifugation column 2 that can be placed in a suitable centrifugation container 3 like a Sarstedt tube 4 or the like. The column 1 is filled with a size exclusion chromatography matrix 5, especially with Biogel P4 or another suitable gel matrix or resin. The gel matrix 5 is equilibrated with a suitable equilibration buffer 6, especially two to three volumes equilibration buffer 6 are used compared to the bed volume of the gel matrix 5. The equilibration buffer 6 only contain components not interfering with the subsequently used endotoxin testing method. The equilibration buffer preferentially comprises a buffer substance that is different from the buffer used in the formulation that is to be tested for endotoxin and comprises at least one bivalent cation. Especially the equilibration buffer 6 may comprise $Ca^{2+}$ and/or $Mg^{2+}$ as bivalent cations in a concentration range between 1 mM and 100 mM. The pH value of the equilibration buffer 6 should be around neutral, preferably between 6.0 and 8.5, most preferably between 7.0 and 8.0. Furthermore, the equilibration buffer 6 may comprise an amphiphilic substance in a concentration below its critical micelle concentration or the concentration of the amphiphilic substance should be equal or below its solubility threshold in the equilibration buffer system, the amphiphilic substance stabilizing monomeric LPS molecules during the phase of aggregate formation. Especially the amphiphilic substance is selected from a group comprising Lauryl alcohol, Tween 20 (Polyethylene glycol sorbitan monolaurate), Polypropylenglycol or SDS (sodium dodecyl sulfate). The equilibration buffer 6 may contain: 20 mM Tris/HCl OR 20 mM HEPES (4-(2-hydroxyethyl)-1-piperazineethanesulfonic acid) at pH 7.4 plus 50 mM NaCl and 20 mM to 50 mM $Ca^{2+}$ and/or $Mg^{2+}$.

For example, a column 1 containing 1.0 ml gel matrix 5 is equilibrated with 2.0 ml to 3.0 ml equilibration buffer 6.

In order to prepare the column 1 for the sample 10 (see FIG. 3), excess equilibration buffer 6* is removed by centrifugation of the column 1 placed within a collection container 3, leaving equilibrated gel matrix 5* within the column 1. This ensures that the sample volume is not increased during the sample preparation described in FIGS. 3 and 4. This equilibration buffer removing centrifugation step is preferentially performed at a centrifugal force of more than 1,500 g, especially at a centrifugal force of about 1,800 g.

According to FIG. 3 a sample 10 of the formulation 11 suspected of comprising an endotoxin or spiked with a known quantity of endotoxin is applied onto the equilibrated gel matrix 5* of the column 1, especially up to 200 µl sample 10 are applied onto a column 1 with 1.0 ml equilibrated gel matrix 5*. The components within the formulation 11 interfering with the endotoxin tests are usually comparatively small molecules with sizes less than 1,500 Dalton. After application of the sample 10 onto the equilibrated gel matrix 5* of the column 1, these small molecules can quickly spread into the equilibrated gel matrix 5*. The endotoxin or LPS is usually present as a high-molecular complex or aggregate, which remains in the exclusion volume of the column 1.

If the formulation 11 comprises a detergent in a concentration above its critical micelle concentration (cmc), the detergent molecules tend to form micelles, thereby integrating LPS/endotoxin into the micelles. This micelle incorporated LPS/endotoxin cannot be detected by the known endotoxin testing methods. The detergent molecules are in a dynamic equilibrium between monomers and micelles. If the formulation 11 is applied onto the column 1, the detergent monomers spread into the equilibrated gel matrix 5* and are not further available for micelle formation. As a result, the LPS/endotoxin is released from the micelles during the centrifugation step can now aggregate with other LPS molecules into high-molecular LPS complexes or LPS aggregates. This LPS aggregation especially takes place in the presence of bivalent cations contained in the equilibration buffer 6, which explains the inhibiting properties of bivalent cation chelators on endotoxin testing methods.

Within the centrifugation container 3 and below the column 1 an endotoxin free collection tube 7 is placed. After another centrifugation step the flow through 15 is collected within the collection tube 7—see FIG. 4. The centrifugation step separates the large LPS complex or aggregate from the small components of the formulation 11. Meanwhile the small components remain within the gel matrix now referenced as 5**, the large LPS complex or aggregate can be found after the centrifugation in the flow through 15. The volume of the flow through 15 exactly corresponds to the volume of the applied sample 10. Therefore, no dilution takes place. The flow through 15 contains also the high molecular components of the sample 10, whereby these high molecular components are now buffered in equilibration buffer 6. Especially the flow through 15 comprises endotoxin in its monomeric and/or its re-aggregated form. This flow through 15 can now be tested for endotoxin.

Hereby, it may be provided that the collected flow through 15 is incubated at a certain temperature for a defined time prior to endotoxin testing to allow equilibrium adjustment between monomeric LPS and aggregated LPS. The equilibrium is located far on the side of the re-aggregated LPS. The incubation time in this step is normally less then 1 h at room temperature.

Figure 7:
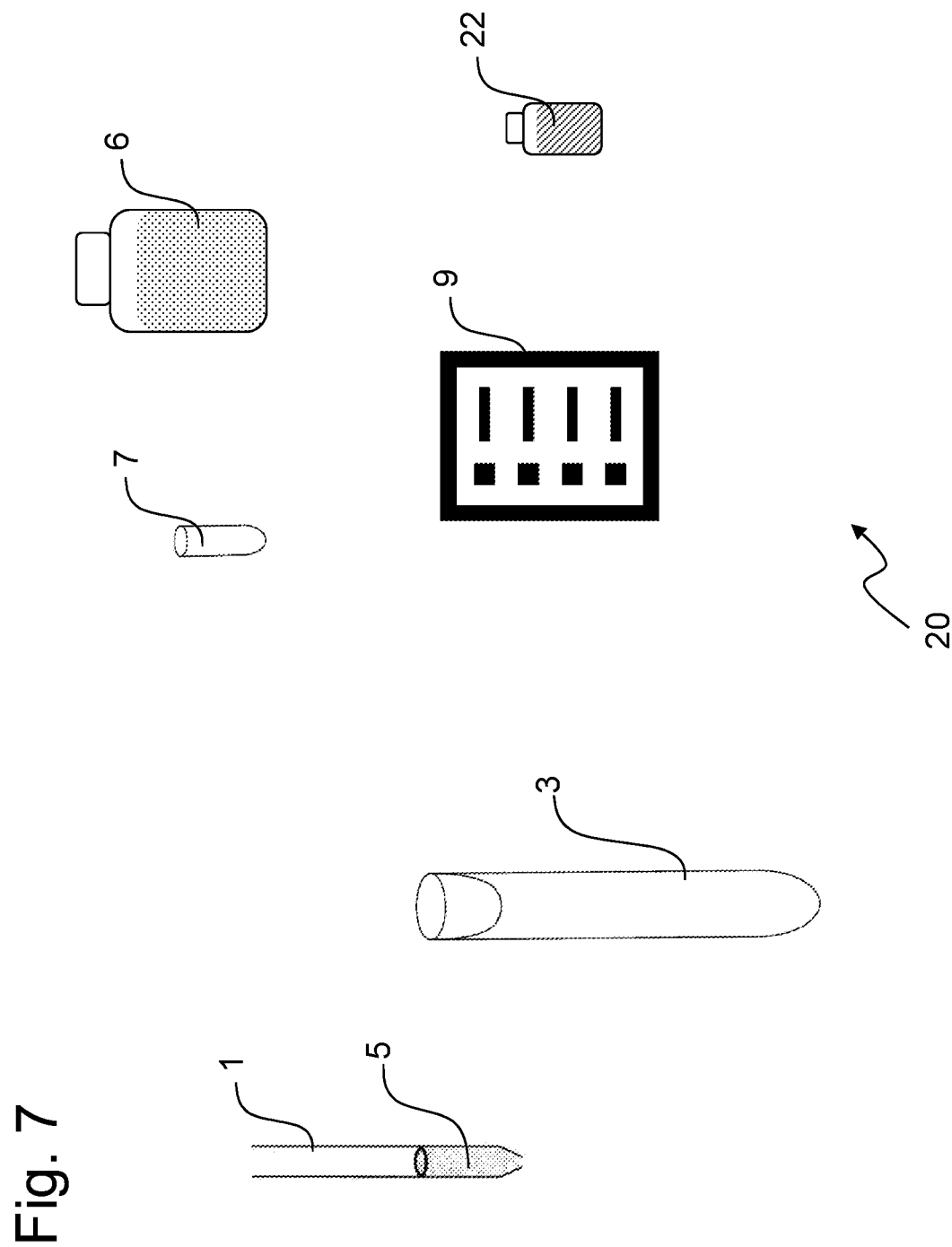
FIG. 7 shows the components of a first embodiment of a kit according to the invention.

FIG. 7 shows the component of a first embodiment of a sample preparation kit 20 according to the invention. The sample preparation kit 20 comprises an endotoxin-free spin column 1 prepacked with a size exclusion chromatography gel matrix 5, a centrifugation container 3, a standard equilibration buffer 6, an endotoxin free collection tube 7 and a user manual 9. The equilibration buffer 6 is used to equilibrate the gel matrix 5 (see FIG. 1) prior to sample preparation according to the explained method. The user manual 9 contains explanations and experimental protocols regarding the method and the individual steps to be performed. The user manual 9 might also give examples for the preparation of other suitable equilibration buffer compositions and provides explanations and hints for selecting the equilibration buffer most suited for the preferred endotoxin testing method.

Furthermore, the sample preparation kit 20 contains an endotoxin sample 22 to be used as positive control.

Even if in the context of the figures there is generally talk of "schematic" representations and views, this does not in any way mean that the representations of figures should be of secondary importance with regards to the disclosure of the invention. The expert is perfectly capable of obtaining enough information from the schematically and abstractly drawn representations to facilitate his understanding of the invention. The figures and experiments thus enable the expert to derive a better understanding of the invention abstractly expressed in the claims and in the general part of the description based on the precise, explained implementations of the method in accordance with the invention and the precise, explained function of the kit components in accordance with the invention.

EXPERIMENTS

General information: For all experiments, where possible, single use materials have been used. All substances have been selected for low endotoxin content and all formulations used were tested for absence of endotoxin. Glassware was either heat-baked (4 h at 200° C.) or treated with 1M NaOH overnight to remove residual endotoxin.

Materials and Instruments used:
USP Reference Standard Endotoxin (RSE) from SigmaAldrich (*E. coli* 0113 LPS, 10,000 EU/vial);
LPS *E. coli* O55:B5, *S. enterica abortus equi*, *S. enterica typhimorium*, *P. aeruginosa* from SigmaAldrich;
Lauryl alcohol and Polypropylenglycol 725 from SigmaAldrich;
Bovine albumin, Bovine IgG highest purity from SigmaAldrich, inhouse LPS-depleted twice by use of Hyglos EndoTrap blue affinity matrix according to manufacturer's instructions (>0.1 EU/mg);
Kinetic Chromogenic LAL Assay (KCA) from Lonza;
EndoZyme, Recombinant Factor C Assay from Hyglos GmbH;
PyroDetect-System, Monocyte Activation Test-MAT from Merck-Millipore;
Sarsted centrifuge tubes, 15 ml PP, sterile, pyrogen-free;
Sarsted reaction tubes, 1.5 ml PP, PCR quality;
Qiagen chromatography columns, 1 ml PP;
Heraeus Multifuge 3SR+, Swing-out rotor 75006445; and
Heidolph Reax Multi, Tube shaker.

Experiment 1: Selection of Suitable Gel Materials

Gel materials used are characterized to have a size exclusion limit below 20,000 Dalton, a generally hydrophilic character and low non-specific interaction capacity. Especially the gel materials are specified as high yield chromatography media. The following gel materials were tested Biogel P2 fine from BioRad, Biogel P4 medium, fine and extra fine from BioRad, Biogel P6 fine and extra fine from BioRad, Biogel P10 fine from BioRad, Sephadex G25 fine and Superdex 30 prep grade, both from GE. The materials were tested for physical stability during centrifugation at 1,800 g. A plus sign (+) was assigned if compression of the gel material was less than 15%, a minus sign (−) was assigned if compression of the gel material was more than 15%. Separation efficiency was tested using with 100 µM 7-amino-4-methyl-coumarin, as described in experiment 2.

TABLE 2

Suitability of different gel materials for the centrifugation assay

| Material (fractionation range) | bead size | Stability | Separation | comment |
|---|---|---|---|---|
| Biogel P2, fine (100-1,800 Da) | 45-90 µm (wet) | + | − | High variation, poor separation, not suitable for the method |
| Biogel P4, medium (800-4,000 Da) | 90-180 µm (wet) | + | − | High variation, not reproducible; not suitable for the method |
| Biogel P4, fine (800-4,000 Da) | 45-90 µm (wet) | + | + | Suitable material for the method |
| Biogel P4, extra fine (800-4,000 Da) | <45 µm (wet) | + | + | Suitable material for the method |
| Biogel P6, fine (1,000-6,000 Da) | 45-90 µm (wet) | + | + | Suitable material for the method |
| Biogel P6, extra fine (1,000-6,000 Da) | <45 µm (wet) | + | + | Suitable material for the method |
| Biogel P10, fine (1,500-20,000 Da) | 45-90 µm (wet) | − | − | Matrix collapsed during centrifugation, poor separation; not suitable for the method |
| Sephadex G25, fine (100-5,000 Da) | 20-80 µm (dry) | − | − | Matrix collapsed during centrifugation, poor separation; not suitable for the method |
| Superdex 30 prep grade (<10,000 Da) | 22-44 µm (wet) | + | + | Suitable material for the method |

Five of the nine tested gel materials showed to be useful for the proposed methods. Inoperative materials either collapse during centrifugation because of low mechanical stability or they show a relatively high variance regarding the fluorescence signal or they leaked too much of the fluorescent dye. For the subsequent experiments Biogel P4 fine was used.

Experiment 2: Gel Bed Volume Versus Separation Efficiency

Optimal bed volume was evaluated using the fluorescent dye 7-Amino-4-methyl-coumarin, furthermore referred to as AMC, for quantification of the separation efficiency. The dye concentration was 100 μM in 20 mM HEPES (4-(2-hydroxyethyl)-1-piperazineethanesulfonic acid), 50 mM NaCl, 2 mM $MgCl_2$, pH 7.2. Two test series were performed, one with 200 μl sample volume and one with 300 μl sample volume. The following centrifugation columns were prepared. All steps were performed at room temperature.

Biogel P4 fine was hydrated with an equilibration buffer containing 20 mM HEPES, 50 mM NaCl, 2 mM $MgCl_2$, pH 7.2 for 30 minutes. The slurry was sucked in a filter funnel and re-suspended with a threefold volume of the equilibration buffer. This procedure was repeated three times. The swelled gel matrix was adjusted to a 50% slurry which was subsequently used to prepare the centrifugation columns with varying bed volumes. The columns were filled using a 5 ml pipette with a disposable tip. Prior to the experiment the excess of equilibration buffer was removed by gravity. The prepared columns were placed in Sarsted tubes in centrifuge buckets. For all the experiments a Heraeus Multifuge 3SR+, Swing-out rotor 75006445 was used. The column was centrifuged with the following settings (see FIGS. 1 and 2).

Acceleration to 1,800 g with profile 4; once the acceleration reached 1,800 g, the centrifuge was immediately stopped.

Deceleration with profile 9

Temperature setting 20° C.

The liquid flow-through of excess equilibration buffer was removed from the Sarsted tubes and small reaction vials were inserted to collect the flow through in the next step (see FIGS. 3 and 4). To each of the columns 200 μl dye solution (series 1) or 300 μl dye solution (series 2) was applied. The buckets were placed in the centrifuge again and the centrifugation was repeated using the same setting as for the first centrifugation step removing excess equilibration buffer. The flow through of the second centrifugation was collected and analysed for volume and fluorescence intensity using a microplate fluorescence reader BioTek Flx800, Ex 380 nm/Em 440 nm and applying 100 μl of the flow through for testing.

Figure 5:
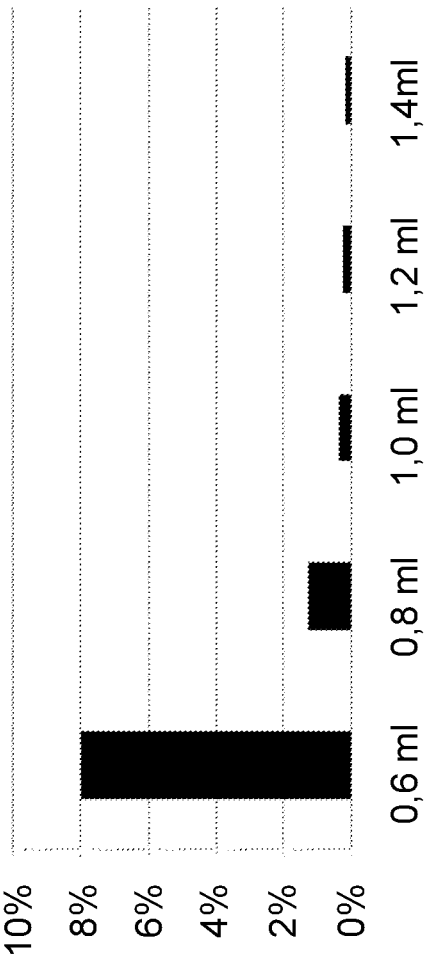
FIG. 5 shows the fluorescence intensity in the flow through of a 200 µl sample depending on used bed volume (see experiment 2).
Figure 6:
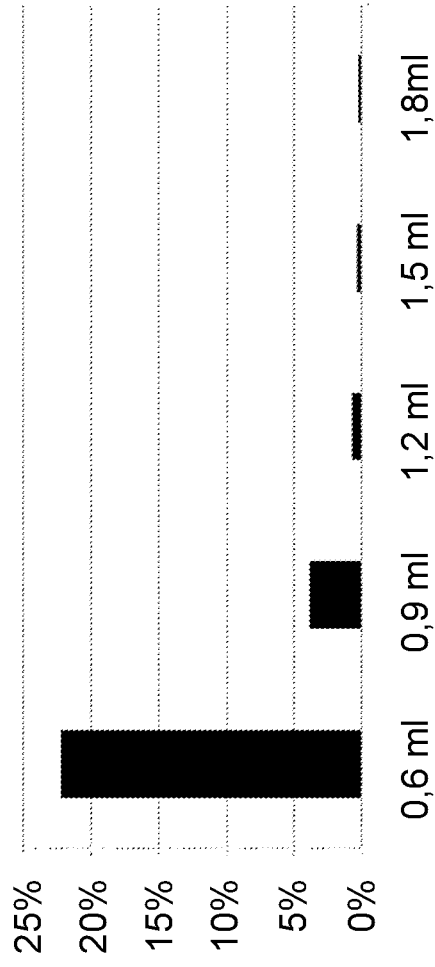
FIG. 6 shows the fluorescence intensity in the flow through of a 300 µl sample depending on used bed volume (see experiment 2).

The results of this experiment are shown in table 3 and displayed in FIGS. 5 and 6, wherein FIG. 5 shows the fluorescence intensity in the flow-through of a 200 μl sample dependent on bed volume from 0.6 ml to 1.4 ml and FIG. 6 shows the fluorescence intensity in the flow-through of a 300 μl sample dependent on bed volume ranging from 0.6 ml to 1.8 ml.

TABLE 3

Different column volumes tested with 200 μl and 300 μl sample volumes and the determined volumes of centrifugation eluate/flow through.

| | bed volume/sample volume recovered | |
|---|---|---|
| | 200 μl Sample | 300 μl Sample |
| 1 | 0.6 ml/202 μl | 0.6 ml/302 μl |
| 2 | 0.8 ml/201 μl | 0.9 ml/308 μl |
| 3 | 1.0 ml/204 μl | 1.2 ml/310 μl |
| 4 | 1.2 ml/203 μl | 1.5 ml/312 μl |
| 5 | 1.4 ml/205 μl | 1.8 ml/314 μl |

It can be seen, that the separation efficiency for the 200 μl AMC solution is >99% at a bed volume of 1 ml and for 300 μl AMC solution a bed volume of 1.5 ml is sufficient to reduce the concentration by a factor of 100. Therefore, when applying a 200 μl sample, the bed volume of the gel matrix should preferentially be at least 1.0 ml and when applying a 300 μl sample, the bed volume of the gel matrix should preferentially be at least 1.5 ml.

Experiment 3: LPS Recovery Versus Gel Bed Volume

The following serial dilutions of LPS 055 were prepared in 20 mM HEPES, 50 mM NaCl, 2 mM $MgCl_2$, pH 7.2 in endotoxin-free glass vials: 20 EU/ml, 4 EU/ml, 0.8 EU/ml, 0.16 EU/ml and 0.032 EU/ml. Between each dilution step the solution was vortexed for 2 minutes at 1,400 rpm using a Heidolph Reax Multi tube shaker. Centrifugation columns according to the procedure of experiment 2 were prepared with a bed volume of 1.5 ml. 300 μl of each dilution was applied and the column was centrifuged at 1,800 g. The flow-through fractions were collected in endotoxin-free plastic cups. For each dilution the flow-through of three columns was pooled (giving 900 μl) and analysed.

The centrifuged samples (50 μl sample+50 μl endotoxin-free water per determination) were analysed in triplicates with three different endotoxin detection methods. Especially Kinetic chromogenic (KCA) LAL from Charles River, EndoZyme from Hyglos GmbH (recombinant Factor C-based fluorescent assay) and, Monocyte Activation Test (MAT) with frozen blood and IL-1B as readout, Pyrodetect System, Merck-Millipore were used. As a comparison and to calculate the recovery, the non-centrifuged dilutions are also analysed. All tests were carried out according to the manufacturer's instruction using the LPS standards supplied with the respective test kits or bought as separate items from the same manufacturer.

Table 4 lists the recovery of LPS 055 after centrifugation through a column filled with 1.5 ml Biogel P4 fine.

TABLE 4

| Recovery of LPS O55 | | | |
|---|---|---|---|
| | LAL | EndoZyme ® | MAT |
| 20 EU/ML | 89 ± 12% | (92 ± 13%) invalid spike control | invalid spike control |
| 4 EU/ml | 95 ± 8% | 87 ± 18% | invalid spike control |
| 0.8 EU/ml | 92 ± 7% | 89 ± 11% | 83 ± 26% |
| 0.16 EU/ml | 82 ± 13% | 95 ± 9% | 80 ± 41% |
| 0.032 EU/ml | 86 ± 14% | 73 ± 15% | below LoD* |
| Average | 89% recovery | 87% recovery | 82% recovery |

*Limit of Detection

In summary, the three tests provide an overall LPS recovery between 82% and 89% showing that LPS can be recovered by centrifugation through the gel material in good yield. For interpretation one should have in mind that according to the acceptance criteria for endotoxin assays results are valid between 50% and 200% of the nominal value. Yields could probably further be increased by optimizing the composition of the gel equilibration buffer. The results of the Monocyte Activation Test are incomplete because of the very narrow dynamic range of the assay and the lower sensitivity of this cell-based assay compared to the other two tests.

Experiment 4: Separation of Inhibitory Substances from Endotoxin

A set of inhibitory substances or physical conditions, especially low and high pH values, was selected to prove the principle capacity of the method to eliminate interfering components from formulations. All formulations listed below were spiked with approximately 25 EU/ml LPS *E. coli* O113. 300 μl of the spiked formulation was either processed according to the methods described herein via a centrifugation column (1.5 ml bed volume, equilibrated with 20 mM HEPES, 50 mM NaCl, 2 mM MgCl$_2$, pH 7.2) or analysed directly using the kinetic chromogenic (KCA) LAL from Charles River. Conditions for preparation, centrifugation and assay are as described in the previous experiments.

80 µl sample plus 20 µl endotoxin-free water was applied in the test (triplicate determination).

20 mM Acetat, 50 mM NaCl, 2 mM MgCl$_2$, pH 4.0
100 mM Na Borat, 50 mM NaCl, 2 mM MgCl$_2$, pH 9.0
20 mM HEPES, 50 mM NaCl, 2 mM MgCl$_2$, 5% Ethanol, pH 7.2
20 mM HEPES, 50 mM NaCl, 2 mM MgCl2, 5% DMSO, pH 7.2
20 mM HEPES, 50 mM NaCl, 2 mM MgCl2, 0.5% SDS, pH 7.2
20 mM HEPES, 50 mM NaCl, 2 mM MgCl2, 0.05% Tween 20, pH 7.2
20 mM HEPES, 50 mM NaCl, 2 mM MgCl2, 0.05% Tween 20, 20 mM Citrat
20 mM HEPES, 50 mM NaCl, 2 mM MgCl2, 2 mM EDTA, pH 7.2
20 mM HEPES, 50 mM NaCl, 2 mM MgCl2, 20 mM Citrat, pH 7.2
20 mM HEPES, 50 mM NaCl, 2 mM MgCl2, 1 mM Benzamidine, pH 7.2
20 mM HEPES, 50 mM NaCl, 2 mM MgCl2, 2 mM PMSF, pH 7.2
20 mM HEPES, 50 mM NaCl, 2 mM MgCl2, 1 mM Chloramphenicol, pH 7.2

Table 5 list the results of the LAL endotoxin determination

TABLE 5

LAL results

| Additive | with centrifugation (method according to invention) | without centrifugation |
|---|---|---|
| No Additive | 18.85 ± 1.44 EU/ml | 20.71 ± 1.28 EU/ml |
| Acetate, pH 4.0 | 17.54 ± 2.34 EU/ml | Invalid spike control |
| Borate, pH 9.0 | 13.06 ± 1.41 EU/ml | 3.39 ± 2.87 EU/ml |
| 5% Ethanol | 18.09 ± 1.89 EU/ml | Invalid spike control |
| 5% DMSO | 16.99 ± 0.83 EU/ml | Invalid spike control |
| 0.5% SDS | 18.17 ± 2.06 EU/ml | 0.38 ± 2.05 EU/ml |
| 0.05% Tween 20 | 17.07 ± 2.68 EU/ml | Invalid spike control |
| 20 mM Citrate, 0.05% Tween 20 | 14.76 ± 0.97 EU/ml | Invalid spike control |
| 2 mM EDTA | 18.20 ± 1.58 EU/ml | Invalid spike control |
| 20 mM Citrate | 15.66 ± 1.73 EU/ml | Invalid spike control |
| 1 mM Benzamidine | 16.43 ± 1.86 EU/ml | Invalid spike control |
| 2 mM PMSF | 12.75 ± 2.31 EU/ml | Invalid spike control |
| 1 mM Chloramphenicol | 19.31 ± 1.95 EU/ml | 4.87 ± 2.62 EU/ml |

The actual amount of the spike was determined to be 20.71 EU/ml. Direct analysis of the formulations with LAL provided mostly invalid results for the spike control or a significant under-determination. After centrifugation, no invalid results occurred and the recovery has been between 12.75 EU/ml (worst) and 19.31 EU/ml (best). This corresponds to 62% (worst) and 93% (best). These results show that adverse effects caused by different chemicals or extreme pH could be substantially reduced by centrifuging the sample through a gel filtration matrix having the capacity to withhold small molecules to very large extend and to let high molecular weight entities to pass the column without significant loss.

Experiment 5: Reconstitution of Endotoxin from Protein Containing Formulation.

Two formulations, each containing a detergent, a chelating substance, especially a buffer, a salt and a protein were spiked with endotoxin. Hereby, RSE=Reference Standard Endotoxin was used. The formulations were incubated in glass vials for 10 days at room temperature of about 20° C. to 24° C. and protected from light.

TABLE 6

Composition of Formulations used in experiment 5

| Component | Formulation 1 | Formulation 2 |
|---|---|---|
| Buffer/Chelator | 20 mM Citrate pH 7.4 | 25 mM Phosphate pH 7.0 |
| Detergent | 0.05% Tween 20 | 0.05% Tween 80 |
| Salt | 50 mM NaCl | 60 mM NaCl |
| Protein | 3.125 mg/ml BSA | 5 mg/ml bovine IgG |
| E.coli LPS O113 (RSE) | 50 EU/ml | 50 EU/ml |

After 10 days the spiked formulations were measured directly using kinetic chromogenic (KCA) LAL from Charles River in dilutions 1:4 and 1:10. Additionally, the same samples (300 µl) were processed using 1.5 ml centrifugation column equilibrated in 20 mM HEPES, 100 mM NaCl, 50 mM MgCl$_2$, pH 7.4. All samples were applied and centrifuged immediately. After centrifugation the eluates were incubated for 60 minutes at room temperature. Dilutions were prepared right before testing, using endotoxin-free water, glass vials and 2 minutes of intensive mixing at about 1,400 rpm.

TABLE 7

Recovery of LPS hidden in formulations according to table 6

|  | without centrifugation (method according to invention) | | with centrifugation | |
|---|---|---|---|---|
|  | 1:4 dilution (recovery) | 1:10 dilution (recovery) | 1:4 dilution (recovery) | 1:10 dilution (recovery) |
| Formulation 1 | 0.34 EU/ml (2.72%) | 0.18 EU/ml (3.60%) | 7.37 EU/ml (58.96%) | 2.15 (EU/ml) (43.00%) |
| Formulation 2 | 0.07 EU/ml (0.56%) | <0.05 EU/ml (<1.00%) | 3.63 EU/ml (29.04%) | 1.22 (EU/ml) (24.4%) |

Two formulations with the capacity to hide spiked LPS from detection by a kinetic chromogenic LAL assay have been evaluated to determine whether separation of the chelator and detergent from the formulation can improve recovery of LPS from the sample. An one hour incubation of the centrifuged sample was included to allow re-association of the LPS complexes. The results listed in table 7 clearly show that centrifugation of the sample according to the method described by the invention provided a substantial improvement of recovery. For the formulation containing citrate, Tween 20 and BSA (bovine serum albumin) the improvement was approximately 22 fold (1:4 dilution) and approximately 12 fold (1:10 dilution), respectively. For the formulation containing phosphate, Tween 80 and IgG the recovery was increased approximately 52 fold (1:4 dilution) and at least 24 fold for the 1:10 dilution. Recovery level within the acceptance criteria of the LAL assay (50-200%) have not yet been achieved in this experiment. However, optimization of an incubation step on the column and an incubation step after centrifugation, especially in view of association kinetics of the LPS as well as optimizing the composition of the equilibration buffer could provide further improvements. This effort must be spent when the method is applied to real pharmaceutical formulations, as it is expected that the optimal equilibration buffer composition will be specific to some extent for different drug formulations and different drug substances.

Experiment 6: Reconstitution of Various Types of LPS

Formulation 2 of experiment 5 (25 mM Phosphate, 0.05% Tween 80, 60 mM NaCl, 5 mg/ml bovine IgG, pH 7.0) or endotoxin-free water containing 0.5 mM $MgCl_2$ was spiked with about 50 EU/ml LPS from 4 different origins.
1) *Escherichia coli* O56:B5
2) *Salmonella abortus equi*
3) *Salmonella enterica* typhimorium
4) *Pseudomonas aeruginosa*

Spiked samples were incubated for 10 days at room temperature (20-24° C.). Two aliquots (200 µl) of each sample were processed, essentially as described in experiment 5. Columns with a bed volume of 1.2 ml were used. The two aliquots of a sample were pooled right after centrifugation and incubated for 1 hour. The spiked water sample was not centrifuged but used to normalize the results for the different LPS materials (taken as 100%). Before endotoxin determinations using the kinetic chromogenic LAL assay (KCA), samples were diluted 1:4 with endotoxin-free water and vortexed for about 2 minutes.

TABLE 8

Recovery of various LPS types

| | | recovery (normalized) | |
|---|---|---|---|
| LPS source | Spiked water | w/o centrifugation | with centrifugation |
| *E. coli* O56:B5 | 100% (48.36 EU/ml) | 0.64% | 53.04% |
| *S. abortus equi* | 100% (60.11 EU/ml) | 2.79% | 82.72% |
| *S. enterica typhimorium* | 100% (32.78 EU/ml) | 0.094% | 37.49% |
| *P. aeroginosa* | 100% (43.50 EU/ml) | 0.33% | 29.78% |

Different LPS types were solubilized in a matrix containing phosphate, tween 80 and IgG and incubated for 10 days at room temperature. Again, recovery of LPS was significantly reduced when using KCA as a detection method without sample preparation (between 0.094% and 2.79% compared to the control). After applying the gel filtration centrifugation step, recovery was between 29.78% and 82.72% for the different LPS types.

Experiment 7: Evaluation of Additives to the Equilibration Buffer for Improving Reconstitution of Solubilized LPS A formulation as described in experiment 5 was prepared under same conditions (Formulation 1), spiked with 50 EU/ml LPS 0113 and incubated for 10 days at room temperature (20-24° C.) to solubilize the spiked LPS.

Different variants of the equilibration buffer were used to prepare three centrifugation columns for each formulation.

TABLE 9

Composition of used equilibration buffers

| Buffer constituents | Var 1 | Var 2 | Var 3 | Var 4 | Var 5 | Var 6 |
|---|---|---|---|---|---|---|
| 20 mM HEPES, pH 7.4 | + | + | + | + | + | + |
| 3.125 mg/ml BSA | + | + | + | + | + | + |
| 100 mM NaCl | + | + | + | + | + | + |
| 50 mM MgCl2 | + | + | + | + | + | + |
| 10 µM Lauryl alcohol | − | + | − | − | − | − |
| 120 µM Tween 20 | − | − | + | − | − | − |
| 10 µM Tween 20 | − | − | − | + | − | − |
| 10 µM Polypropylenglycol 725 | − | − | − | − | + | − |
| 10 µM SDS | − | − | − | − | − | + |

After removing the excess of equilibration buffer by centrifugation at 1,800 g, triplicates of each variant were applied to the columns. The samples were incubated on the columns for 5 minutes at room temperature prior to the second centrifugation. The eluates of the centrifugation were incubated for 60 minutes at room temperature. Afterwards a 1:4 dilution of each sample was prepared in glass vials with 2 minutes of intensive vortexing (1,400 rpm). Samples were tested using the LAL assay (KCA).

TABLE 10

Improvement of recovery applying additives to the equilibration buffer:

| Formulation Variant | Endotoxin value (EU/ml and % recovery) |
|---|---|
| Variant 1 (Control) | 6.07 EU/ml (48.56% recovery) |
| Variant 2 (10 µM Lauryl alcohol) | 8.61 EU/ml (68.88% recovery) |
| Variant 3 (120 µM Tween 20) | 0.63 EU/ml (0.48% recovery) |
| Variant 4 (10 µM Tween 20) | 9.25 EU/ml (74.00% recovery) |
| Variant 5 (10 µM Polypropylenglycol 725) | 7.80 EU/ml (62.40% recovery) |
| Variant 6 (10 µM SDS) | 6.83 EU/ml (54.64% recovery) |

Selected amphiphilic substances were added to the equilibration buffer in order to show, that reconstitution of LPS to complexes during or after the separation by gel filtration can be improved by supplementation of the equilibration buffer. Compared to variant 1 (control), the addition of lauryl alcohol (Var.2), Tween 20 (Var.4), Polypropylenglycol 725 (Var.5) and SDS (Var.6) when used well below their critical micelle concentration (cmc), provided equal or increased LPS recovery. Only Tween 20 (Var. 3) used at twice the critical micelle concentration (cmc) provided very low recovery compared to the control. This experiment is indicative that further principles, besides high magnesium ion concentration, when added to the equilibration buffer could improve the overall recovery of the process.

The invention has been described with reference to preferred embodiments. To the expert it is also conceivable, however, to make changes and modifications without leaving the scope of protection of the appended claims.

LIST OF REFERENCE NUMBERS 1 column
2 endotoxin-free centrifugation column
3 centrifugation container
4 Sarstedt tube
5 size exclusion chromatography matrix; gel matrix 5* equilibrated gel matrix
5** gel matrix buffered with the low molecular weight components of the formulation
6 equilibration buffer
6* excess equilibration buffer
7 collection tube
9 user manual
10 sample
11 formulation
15 flow through
20 sample preparation kit
22 endotoxin sample

I claim:

1. A method for evaluation of Low Endotoxin Recovery (LER) effects in a pharmaceutical formulation and/or for an elaboration of a composition of a suitable equilibration buffer (6), comprising:
spiking an undiluted sample of a pharmaceutical formulation with a known activity of a lipopolysaccharide (LPS) standard,
testing an aliquot of the spiked sample for endotoxin,
if the spiked sample shows a test result corresponding to less than 50% of the known activity of the lipopolysaccharide (LPS) standard spiked into the sample, then applying aliquots of the spiked sample to at least two endotoxin-free centrifugation columns (2), wherein the centrifugation columns (2) containing a size exclusion chromatography matrix (5) and each of the at least two endotoxin-free centrifugation columns (2) having been equilibrated with different equilibration buffers (6);
eluting a flow through (15) from each centrifugation columns (2) by centrifugation, which flow through (15) can then be used for endotoxin determination; and
selecting the equilibration buffer (6) best suited for lipopolysaccharide recovery for the given pharmaceutical formulation based on the results of the endotoxin determination.

2. The method of claim 1, wherein the results of the endotoxin determination are compared to an aliquot of the non-centrifuged spiked sample and a positive water control.

3. The method of claim 1, further comprising incubating the undiluted sample of the given pharmaceutical formulation spiked with a known activity of the lipopolysaccharide (LPS) standard at a temperature for a time period prior to endotoxin testing step.

4. The method of claim 3, wherein the incubating step is performed between 1° C. and 37° C.

5. The method of claim 3, wherein the incubating step is performed at about 4° C. or wherein the incubating step is performed at a room temperature between 18° C. and 24° C.

6. The method of claim 3, wherein the incubating step is performed for at least 1 h.

7. The method of claim 3, wherein the incubating step is performed for between 24 h and 168 h.

8. The method of claim 1, wherein the size exclusion chromatography matrix (5) has a size exclusion volume or exclusion cut-off within the range of 2000 Dalton to 20000 Dalton.

9. The method of claim 8, wherein the size exclusion chromatography matrix (5) has a size exclusion volume or exclusion cut-off within the range of 4000 Dalton to 7000 Dalton.

10. The method of claim 9, wherein the size exclusion chromatography matrix (5) has a size exclusion volume or exclusion cut-off below 6000 Dalton.

11. The method of claim 1, wherein the size exclusion chromatography matrix (5) is an uncharged, hydrophilic gel matrix or wherein the size exclusion chromatography matrix (5) is a crosslinked polyacrylamide gel matrix, and wherein the size exclusion chromatography matrix (5) has a high mechanical stability at centrifugation forces of up to 1800 g.

12. The method of claim 1, wherein the equilibration buffer (6) comprises a buffer substance, different from the buffer used in a formulation (11) that is to be tested for endotoxin presence and wherein the equilibration buffer (6) comprises at least one bivalent cation.

13. The method claim 12, wherein the equilibration buffer (6) comprises $Ca^{2+}$ or $Mg^{2+}$ as bivalent cation, or wherein the pH of the equilibration buffer (6) is 6.0 to 8.5.

14. The method of claim 13, wherein the equilibration buffer (6) comprises $Ca^{2+}$ or $Mg^{2+}$ in a concentration between 1 mM and 100 mM.

15. The method of claim 13, wherein the equilibration buffer (6) comprises $Ca^{2+}$ or $Mg^{2+}$ in a concentration between 1 and 50 mM and wherein the pH of the equilibration buffer (6) is between 7.0 and 8.0.

16. The method of claim 13, wherein the equilibration buffer (6) comprises $Ca^{2+}$ or $Mg^{2+}$ in a concentration between 20 and 50 mM and wherein the pH of the equilibration buffer (6) is between 7.0 and 8.0.

17. The method of claim 1, wherein the equilibration buffer (6) comprises an amphiphilic substance in a concentration below its critical micelle concentration, or equal or below its solubility threshold in the equilibration buffer (6).

18. The method of claim 16, wherein the amphiphilic substance is selected from a group comprising Lauryl alcohol, Tween 20, Polypropylenglycol or SDS.

* * * * *